United States Patent
Osborne et al.

(10) Patent No.: US 8,267,874 B2
(45) Date of Patent: Sep. 18, 2012

(54) LOW FRICTION COATED MARKED WIRE GUIDE FOR OVER THE WIRE INSERTION OF A CATHETER

(75) Inventors: Thomas A. Osborne, Bloomington, IN (US); Andrew K. Hoffa, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 145 days.

(21) Appl. No.: 12/574,124

(22) Filed: Oct. 6, 2009

(65) Prior Publication Data

US 2010/0021619 A1    Jan. 28, 2010

Related U.S. Application Data

(62) Division of application No. 10/831,740, filed on Apr. 23, 2004, now Pat. No. 7,651,469.

(60) Provisional application No. 60/465,712, filed on Apr. 25, 2003.

(51) Int. Cl.
*A61M 25/00* (2006.01)
(52) U.S. Cl. .................................................. 600/585
(58) Field of Classification Search .................. 600/585; 604/164.13
See application file for complete search history.

(56) References Cited

U.S. PATENT DOCUMENTS

| | | | |
|---|---|---|---|
| 4,951,686 | A | 8/1990 | Herlitze |
| 5,084,022 | A | 1/1992 | Claude |
| 5,379,779 | A | 1/1995 | Rowland et al. |
| 5,860,923 | A | 1/1999 | Lenker et al. |
| 6,027,863 | A | 2/2000 | Donadio, III |
| 6,033,720 | A | 3/2000 | Stoltze et al. |
| 6,059,738 | A | 5/2000 | Stoltze et al. |
| 6,078,832 | A | 6/2000 | Lenker et al. |
| 6,106,889 | A | 8/2000 | Beavers et al. |
| 6,254,550 | B1 | 7/2001 | McNamara et al. |
| 6,428,512 | B1 | 8/2002 | Anderson et al. |
| 2002/0087098 | A1 | 7/2002 | Iwami et al. |
| 2004/0039304 | A1 | 2/2004 | Connors, III et al. |

FOREIGN PATENT DOCUMENTS

WO    WO 97/42910    11/1997

*Primary Examiner* — Jeffrey G Hoekstra
(74) *Attorney, Agent, or Firm* — Brinks Hofer Gilson & Lione

(57) ABSTRACT

A wire guide includes a mandrel that has a proximal portion and a distal portion. A coating having a low coefficient of friction is disposed on at least part of the proximal portion and the distal portion of the mandrel, where a part of the proximal portion and distal portion of the mandrel without the coating indicates a marking on the wire guide. This marking on the wire guide allows a user to determine a trimmable length of a catheter, and the low friction coating enables the user to easily advance the catheter over the wire guide.

17 Claims, 2 Drawing Sheets

LOW FRICTION COATED MARKED WIRE GUIDE FOR OVER THE WIRE INSERTION OF A CATHETER

CROSS-REFERENCE TO RELATED APPLICATIONS

This application is a divisional of U.S. patent application Ser. No. 10/831,740, filed Apr. 23, 2004 now U.S. Pat. No. 7,651,469, entitled "LOW FRICTION COATED MARKED WIRE GUIDE FOR OVER THE WIRE INSERTION OF A CATHETER", which claims the benefit of U.S. Provisional Patent Application Ser. No. 60/465,712, filed Apr. 25, 2003, each of which is hereby incorporated by reference in its entirety.

BACKGROUND OF THE INVENTION

The present invention relates to wire guides used for percutaneous placement of catheters and other medical devices in the vasculature of a patient.

A wire guide can be used for percutaneous placement of a catheter into a vascular system. The wire guide has a proximal end that is held by a physician and a distal end that is inserted into the vascular system. In use a physician inserts an introducer needle with the wire guide into a vessel, e.g., a brachial vein, a cephalic vein. The wire guide is introduced through the introducer needle into the vessel to a part of the vascular anatomy at which the physician is performing an interventional or diagnostic procedure. The needle is then withdrawn over the wire guide and a catheter placed over the wire guide. A physician holds a proximal portion of a catheter as a distal portion of the catheter is inserted over the wire guide. The physician may use one of many types of catheters or medical devices with the wire guide to perform the procedure, such as a peripherally inserted central catheter (PICC) line.

When a wire guide is percutaneously introduced into a vessel of the patient, the physician verifies that a suitable portion of the catheter or other medical device will be inserted over the wire guide to a precise location in the vasculature of the patient. If a relatively large portion of the catheter remains outside of the patient's body, the catheter may be caught on outside objects, affecting the placement of the catheter and causing the patient to experience discomfort. Typically, in order to limit the patient's discomfort, the wire guide in the vessel of the patient is extracted from the vessel with a clamp attached to the proximal portion of the wire guide remaining outside of the patient's body. The catheter is then placed side by side next to the wire guide and the proper amount of a distal portion of the catheter is cut or trimmed away. The trimmed distal portion of the catheter is cut according to marks on the wire guide which indicate a length of the wire guide inserted into the patient. The trimmed catheter may then be inserted into the patient over the guide wire to the location in the vasculature or by using a stiffening wire inside the catheter and advancing the catheter without use of the wire guide. This procedure is generally time consuming because it requires the physician insert the wire guide, withdraw the wire guide, cut the distal portion of the catheter and insert the catheter into the patient, although it ensures that only a small proximal portion of the catheter will be left outside of the patient's body during the interventional procedure.

Another method has been developed to insert a PICC over a wire guide into a patient, wherein a relatively longer length wire guide is used. The wire guide has marks on the distal end at 60 centimeter (cm) that allow the user to determine the length of the catheter that must be trimmed by looking at the marks that are remaining outside of the patient's body. However, most of the materials used for these PICC lines include silicone and urethane, which may not allow the catheter to be easily advanced over the wire guide due to friction resistance. In addition, the utilization of these PICC line materials can lengthen the time of this procedure, causing undesired difficulty and discomfort.

Therefore, there is a need for an apparatus and a method that enables a user to quickly and easily advance a catheter over a wire guide, assisting in the determination of where the catheter should be trimmed with relatively low resistance.

BRIEF SUMMARY OF THE INVENTION

One embodiment of the present invention provides a wire guide that allows a user to easily advance a catheter over a wire guide and assists in the determination of where the catheter should be trimmed.

In another embodiment of the invention, a wire guide comprises a mandrel and a coating having a low coefficient of friction disposed on at least a segment of the mandrel. Each segment has a depth mark indicated by an area of coating at least partially removed from the mandrel. This marking on the wire guide allows a user to determine a trimmable length of the catheter, and the low friction coating enables the user to easily advance the catheter over the wire guide.

One method of making a wire guide is also disclosed. A mandrel having a proximal portion and a distal portion is provided. A coating having a low coefficient of friction is applied over at least a portion of the mandrel. At least one portion of the coating is removed from the mandrel to provide a marking on the wire guide.

Further aspects, features, and advantages of the invention will become apparent from consideration of the following description and the appended claims when taken in connection with the accompanying drawings.

BRIEF DESCRIPTION OF THE DRAWINGS

FIG. 3 is a side cross-sectional view of a wire guide in accordance with another embodiment of the present invention.

DETAILED DESCRIPTION OF THE INVENTION

The presently preferred embodiments of the invention are described with reference to the drawings. The descriptions of the preferred embodiments are exemplary and are not intended to limit the scope of the invention.

Figure 1:
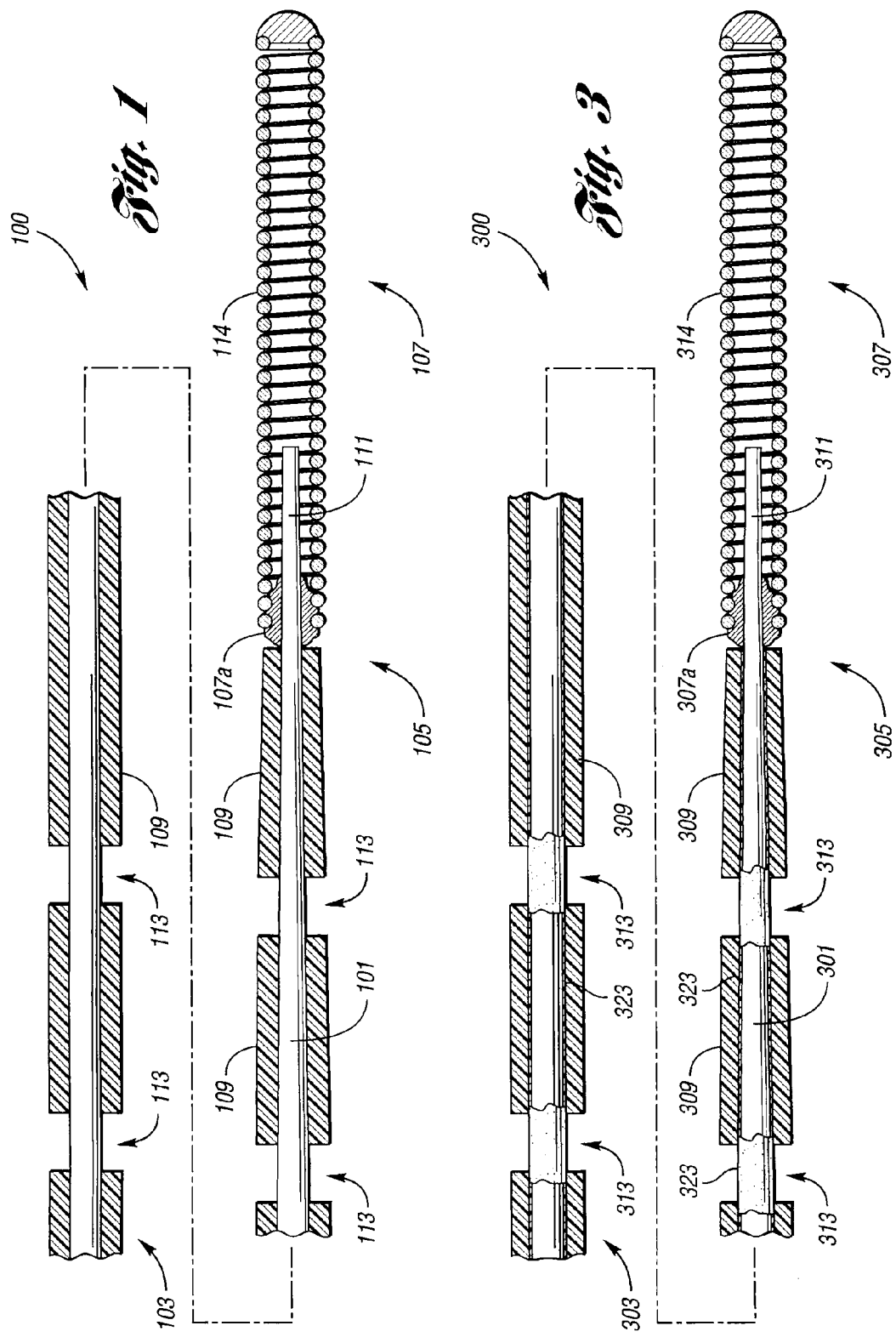
FIG. 1 is a side cross-sectional view of a wire guide with depth marks in accordance with one embodiment of the present invention.

In accordance with one embodiment of the present invention, FIG. 1 illustrates a wire guide 100 generally comprising a mandrel 101, a coating 109 disposed about the mandrel 101 and wire guide depth markings 113. More specifically, the mandrel 101 has a proximal portion 103 extending to a distal portion 105. As shown, distal portion 105 includes tapered portion 111 to which a coil 107 is attached, defining a distal tip of the wire guide 100. In this embodiment, the coil 107 is attached to the distal tip 105 by a solder joint 107a. Coating 109 is disposed on at least segments of the proximal portion 103 and the distal portion 105. In this embodiment, each segment has a depth mark indicated by an area of coating at least partially removed from the mandrel 101. The depth mark allows a physician to assess the length to trim or cut a catheter to be used for over the wire insertion to a location in the vasculature of a patient.

In this embodiment, the wire guide 100 has a generally cylindrical shape. This shape helps a user maneuver the wire guide 100 through a vessel, e.g., a brachial vein or a cephalic vein, of a patient. The wire guide 100 may have a length ranging from about 40 centimeters (cm) to about 480 cm and an outside diameter ranging from about 0.008 inch to about 0.05 inch plus the thickness of coating 109. Preferably, the wire guide 100 has an outside diameter of about 0.018 inch.

The mandrel 101 may be made of Nitinol—a nickel-titanium alloy, although it may be made of any suitable material. The mandrel is preferably made of a flexible or bendable material that is substantially flexible to traverse vessels of a patient. Of course, the mandrel 101 may be made of any suitable material that has properties similar to stainless steel and Nitinol, such as kink resistance, the ability to withstand sterilization (heat and moisture), and being non-toxic.

The mandrel 101 may have a diameter of between about 0.008 inch and about 0.050 inch. Preferably, the mandrel 101 has a diameter of about 0.018 inch. The proximal portion 103 may have a length ranging from about 20 cm to about 300 cm. At least a portion of the proximal portion 103 and the distal portion 105 may be covered by a coating 109. Coating 109 may include any suitable material, such as a polymer, that has a low coefficient of friction and provides a reduction in friction between an inner diameter of the catheter and the outer diameter of the wire guide. The coating 109 may symmetrically cover the mandrel 101. A segment of the proximal and distal portions 103 and 105 covered by the low friction coating may range in length from about 1 cm on the mandrel 101 to nearly the entire mandrel. The low friction coating 109 is preferably used to allow a physician to grasp the handle of the proximal portion 103 securely, but low enough to easily slide a catheter over the wire guide 100.

The low friction coating 109 may have a coefficient of friction in the range of about 0.01 to about 0.9. Preferably, the coating 109 is a polytetrafluroethylene (TEFLON) material that may have a typical TEFLON (polytetrafluoroethylene) color. TEFLON (polytetrafluoroethylene) has a coefficient of friction of about 0.6. The coating 109 may also be PARALENE—poly(para-xylylene). The coating 109 may also be an opaque hydrophilic coating that is colored. The hydrophilic coating 109 has a polished or slick surface and a coefficient of friction in the range of about 0.01 to 0.05 to allow the wire guide 100 to be easily maneuvered through the vasculature. The thickness of the coating 109 is preferably in the range of about 0.0001 inch to about 0.003 inch.

In an alternative embodiment, a translucent mask may cover the mandrel 101 before it is covered with the coating 109. The mask would be applied to mandrel 101 before the coating 109 to prevent coating 109 from sticking to selected areas of the proximal portion 103 and distal portion 105 of the mandrel 101. The coating 109 is then applied to segments of the proximal portion 103 and distal portion 105. In this embodiment, the masked area(s) indicate depth marking(s) 113.

In another embodiment, selected areas of the mandrel 101 may be brightened by buffing or electro-polishing before the mandrel is covered with the coating 109. The brightening of mandrel 101 would enhance the visibility of depth markings 113 on the mandrel 101 such that even if the wire guide 100 generally may not be visible to a physician, at least the depth markings 113 would still be visible to the physician.

At least one portion of the coating 109 may also be removed from the wire guide 100 to form depth markings 113. Portions of coating 109 are removed from the wire guide 100 to form depth markings 113, which are used to facilitate trimming or cutting of a segment of the distal portion of the catheter. The wire guide 100 with the depth markings 113 is inserted into a vessel, e.g., a brachial vein or a cephalic vein, of a patient, and then the catheter is slid over the wire guide 100 so that the catheter may remove or deliver any fluid or medication in the vessel.

The depth markings 113 on the wire guide 100 assist the physician or user in determining a length of the catheter to be used before it is placed over the wire guide 100. A physician matches the depth markings 113 with the typical markings on a catheter. The catheter is typically marked at 5 cm increments after a first 20 cm marking from a distal tip of the catheter up to a last marking at 60 cm. Prior to inserting the catheter into a desired position over the wire guide, the physician assesses the portion of the distal end of the catheter that is to be trimmed by utilizing the depth markings on the wire guide and catheter. The trimmed catheter provides precision in placement of the catheter to location in the vessel with a minimal amount of catheter being left outside the body. In this embodiment, the wire guide 100 is marked at about every 5 cm to 20 cm, and at the 60 cm marking there are three separate 2 millimeter (mm) long markings to indicate the end of the marking. As stated above, the distal portion of the catheter is trimmed based on the depth markings 113 of the wire guide 100, so a precise length of catheter may be utilized, reducing discomfort to the patient. Typically, the catheter is trimmed by a physician with a scalpel included with a catheter set. Of course, the catheter may be trimmed by use of any other conventional methods and devices. The depth markings 113 allow a user to peripherally insert and centrally place a distal tip of the catheter at a desired position over the distal portion 105, such as a right atrium of a patient's heart. Depth markings 113 allow the user to precisely trim the length of the distal portion of the catheter for accurate placement in the vasculature of a patient and minimal length outside of the patient.

The amount of coating 109 removed from the wire guide 100 is preferably between about 0.0002 inch to about 0.003 inch. In an alternative embodiment, a portion of the amount of coating 109 removed is in the range of about 0.0006 inch to about 0.0011 inch. Each of the markings 113 has a depth into the wire guide 100 of about 0.0001 inch to about 0.0005 inch depending on the thickness of the coating 109. The amount of coating 109 removed is the portion used to distinguish the wire guide 100 from the coating 109. Along the wire guide 100, at increments of about 5 cm, the coating 109 can be removed at various lengths on the wire guide 100 to form the depth markings 113 to match the depth marking 113 with the typical markings on the catheter as described above. The increments along the wire guide 100 are about 5 cm to 20 cm. The lengths of the increments are about 1 mm to 3 cm. For example, a 2 cm length and 0.0001 inch depth of coating 109 may be removed from a midpoint of the proximal portion 103 and distal portion 105 of the wire guide 100. In another example, a 1 mm length and 0.0005 inch depth of coating may be removed from a 60 cm distal portion 105 of the wire guide 100. In an alternative embodiment, if a portion of the coating 109 is removed from a brightened mandrel 101 then the depth marking 113 would reveal the brightened portion of the mandrel as a marking.

The coil or tip coil 107 is preferably connected to the tapered portion 111 of the mandrel 101 by a solder joint 107a. The coil 107 may surround or cover a part of the distal portion 105. Any other type of suitable connection may be used in place of the solder joint 107a, such as an adhesive, glue or a connection device to connect the coil 107 to the tapered portion 111. Coil 107 may be radiopaque and made of Nitinol, platinum, platinum alloy, stainless steel or any other suitable material. In an alternative embodiment, coil 107 may be covered by the coating 109, portions of which may be removed to show depth markings 113. The coating 109 covering the coil 107 is used to increase the slickness of coil 107 to allow it to maneuver more easily through the vessel.

Figure 2:
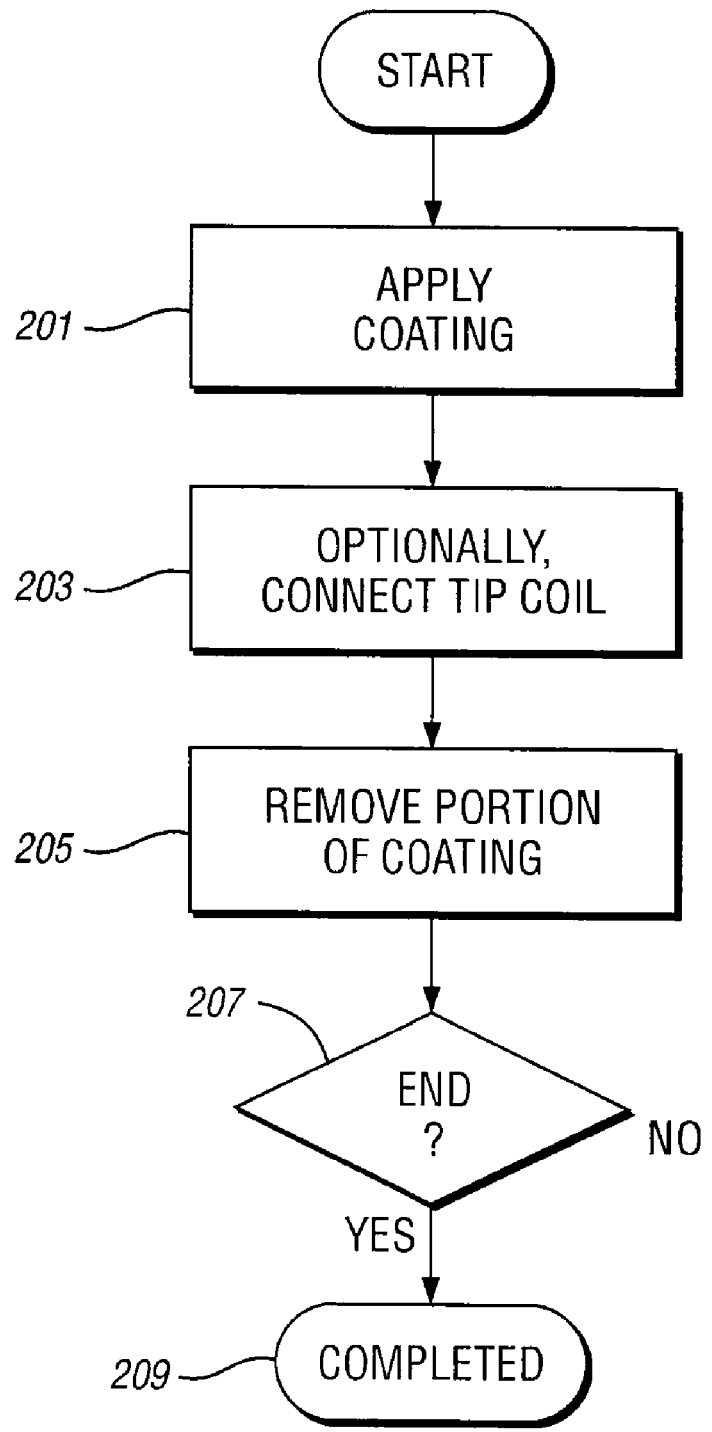
FIG. 2 is a flow chart of a method of manufacturing the wire guide in accordance with the wire guide of FIG. 1.

As shown in FIG. 2, the present invention also includes a method of making a wire guide. At block 201, a coating 109 is applied over at least a part of the proximal portion 103 and the distal portion 105 of the mandrel 101. Parts of the proximal portion and the distal portion without the coating indicate a depth marking 113 on the wire guide 100. The coating 109 preferably comprises a material such as TEFLON (polytetrafluoroethylene), a hydrophilic coating, PARALENE—poly(para-xylylene) or any suitable low friction polymer. Preferably, the coating 109 fully coats the proximal portion 103 and the distal portion 105 of the mandrel 101. In an alternative embodiment, the coating 109 may be selectively applied to at least one segment or portion of the proximate portion 103 and the distal portion 105 of the mandrel 101. The coating 109 may also be applied in between, such as a portion between, the proximal portion 103 and distal portion 105 of the mandrel 101. The coating 109 may be applied to the mandrel 101 by dipping, spraying, over-extruding or by using any other suitable coating method. Over-extruding involves melting the coating, and passing the mandrel 101 through an extruder so that the melted coating 109 covers or envelops the mandrel 101. Alternatively, the coating 109 is applied over mandrel 101 by spraying or die wiping. In another alternative embodiment, a polymer material, such as PARALENE (poly(para-xylylene)) is vapor deposited over mandrel 101.

The coating 109 may be applied to at least one segment along the proximal portion 103 and distal portion 105, wherein a segment along the proximal portion 103 and the distal portion 105 with at least a portion of the coating removed indicates the depth marking 113 of the wire guide. In still yet another alternative embodiment, the mandrel 101 may be brightened by a typical buffing or electropolishing method before coating 109 is applied. As stated above, the brightening of mandrel 101 would enhance the visibility of the depth marking 113 on the wire guide 100.

Optionally, at block 203, a coil 107 is connected to the tapered portion 111 of the mandrel 101. Preferably, the coil 107 is soldered to the tapered portion 111 by a solder joint 107a as previously described.

At block 205, at least one portion of the coating 109 is removed from the wire guide 100 to form the depth markings 113. The coating is removed by any suitable process, such as grinding, etching, abrading etc. Preferably, a grinding process is utilized to remove the coating 109 to form the depth markings 113 of the wire guide 100. In an example, the wire guide 100 may be rotated while it is in contact with a typical grinding wheel on a typical bench grinder, where the grinding wheel removes a portion of the coating 109. In another example, the wire guide 100 may be placed in an automated system that grinds into the wire guide 100 to a specific depth. In either of the examples, about 0.0006 inch to about 0.0011 inch portions of the coating 109 or the full coating of 0.0002 inch to about 0.003 inch is ground away from one or more locations at one or more lengths at about 5 cm to 20 cm on the wire guide 100 to distinguish the wire guide 100 from coating 109. The grinding process may provide a bright metal mark against a dull polymer or opaque hydrophilic coating 109. The advantage of using the grinding system is that it can be continued down into the surface of the coating 109 producing a bright mark on wire guide 100 that contrasts better with the surrounding coating 109.

At block 207, the process of removing a portion of coating 109 to provide the markings 113 may end or continue depending on whether another depth marking is to be added to the wire guide 100. If another depth marking is desired, then this process may continue at 201. If another depth marking is not needed, then this process is completed at block 209.

In yet another embodiment as shown in FIG. 3, a mandrel includes a mask 323 is disposed between the mandrel 301 and coating 309. In this embodiment, mask 323 may be applied over the mandrel 301 before coating 309 is applied. The wire guide 300 includes similar components as the wire guide 100 discussed above. For example, the mandrel 301, proximal portion 303, distal portion 305, coating 309, and depth markings 313 are similar to the mandrel 101, proximal portion 103, distal portion 105, coating 109, and depth markings 113 of wire guide 100. The mask 323 may be applied on the mandrel 301 prior to applying the coating 309 to prevent the coating 309 from sticking to the selected areas of the mandrel 301. The coating then may be removed from the wire guide 300 with greater ease as discussed below. Of course, the mask 323 may also be removed as well without falling beyond the scope or spirit of the present invention.

As described above, the wire guides 101 and 301 are covered with a material that has a low coefficient of friction. A portion of the covering is removed to indicate a marking on the wire guide, which facilitates the accurate trimming of a catheter. This marking enables a user to determine a trimmable length of the catheter, while the low friction coating allows the easy advance of the catheter over the wire guide.

It is therefore intended that the foregoing detailed description be regarded as illustrative rather than limiting, and that it be understood that it is the following claims, including all equivalents, that are intended to define the spirit and scope of this invention.

We claim:

1. A method of making a wire guide for insertion of a catheter into a patient's vasculature, the method comprising the steps of:
    applying a coating having a low coefficient of friction over at least a portion a mandrel having a proximal portion and a distal portion; and
    removing at least one pair of first portions of the coating from the mandrel to provide depth markings on the wire guide leaving a second portion of the coating between the first portions of each pair, wherein the second portion of the coating disposed between the first portions of each pair is not removed from the mandrel, the second portion having a length between about 5 cm and 20 cm, the depth markings being configured to assist a user of the wire guide in determining a length of catheter to be inserted into the patient's vasculature.

2. The method of claim 1 wherein the coating comprises a Teflon material.

3. The method of claim 1 wherein the coating comprises a hydrophilic material.

4. The method of claim 1 wherein the coating comprises a Paralene material.

5. The method of claim 4 further comprising the steps of applying the Paralene material by using a vapor deposition process.

6. The method of claim 1, further comprising the step of connecting a coil to the distal portion of the mandrel.

7. The method of claim 6 wherein connecting the coil further comprises soldering the coil to the distal portion of the mandrel.

8. The method of claim 1 wherein the at least two first portions have a plurality of lengths.

9. The method of claim 1 wherein removing the at least two first portions of the coating comprises removing a section of coating located at a halfway point between the proximal and distal portions of the mandrel.

10. The method of claim 1 wherein the mandrel comprises a stainless steel material.

11. The method of claim 1 wherein the mandrel comprises a nickel-titanium alloy material.

12. The method of claim 1 wherein the coating comprises a polymer material.

13. The method of claim 6 wherein the distal portion comprises a tapered portion connected to the coil.

14. The method of claim 1 wherein the at least one pair of first portions of the coating are removed by a grinding process.

15. The method of claim 1 wherein applying the coating further comprises dipping the proximal and distal portions of the mandrel.

16. The method of claim 1 wherein applying the coating further comprises spraying the coating onto the proximal and distal portions of the mandrel.

17. A method of making a wire guide, the method comprising the steps of:
    applying a coating having a low coefficient of friction over at least a portion a mandrel having a proximal portion and a distal portion;
    removing at least one pair of first portions of the coating from the mandrel to provide depth markings on the wire guide leaving a second portion of the coating between the first portions of each pair, wherein the second portion of the coating disposed between the first portions of each pair is not removed from the mandrel, the second portion having a length between about 5 cm and 20 cm; and
    applying a distinguishable end marking.

* * * * *